United States Patent
Li et al.

(10) Patent No.: US 9,028,544 B2
(45) Date of Patent: May 12, 2015

(54) ROBOTIC HEART VALVE ANNULUS SIZER

(75) Inventors: XueMei Li, Shoreview, MN (US); Jack Lemmon, St. Paul, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 826 days.

(21) Appl. No.: 13/148,168

(22) PCT Filed: Feb. 1, 2010

(86) PCT No.: PCT/US2010/000273
§ 371 (c)(1),
(2), (4) Date: Dec. 8, 2011

(87) PCT Pub. No.: WO2010/090720
PCT Pub. Date: Aug. 12, 2010

(65) Prior Publication Data
US 2012/0071968 A1   Mar. 22, 2012

Related U.S. Application Data

(60) Provisional application No. 61/206,970, filed on Feb. 6, 2009.

(51) Int. Cl.
*A61F 2/24* (2006.01)
*A61B 5/107* (2006.01)

(52) U.S. Cl.
CPC ............. *A61F 2/2496* (2013.01); *A61B 5/1076* (2013.01)

(58) Field of Classification Search
CPC .......................... A61F 2/2496; A61B 5/1076
USPC ............. 606/1, 148, 150; 600/587; 623/2.11, 623/2.36, 2.38, 2.37
See application file for complete search history.

(56) References Cited

U.S. PATENT DOCUMENTS 5,290,300 A * 3/1994 Cosgrove et al. ............. 606/148
6,001,127 A * 12/1999 Schoon et al. ............... 623/2.11
(Continued)

FOREIGN PATENT DOCUMENTS

JP          06-509489 A    10/1994
JP          2002518089 A    6/2002
(Continued)

OTHER PUBLICATIONS

International Search Report, PCT/US2010/000273, dated Apr. 28, 2010.
(Continued)

*Primary Examiner* — Julian W Woo
*Assistant Examiner* — Lucas Paez
(74) *Attorney, Agent, or Firm* — Lerner, David, Littenberg, Krumholz & Mentlik, LLP

(57) ABSTRACT

A heart valve annulus sizer is provided for measuring a valve to be fitted with an annuloplasty ring. The sizer may include a body having a peripheral portion defining an opening, at least one rib disposed within the opening and dividing the opening into at least a first opening and a second opening, and an anchor disposed on and projecting from the body. The sizer may include a length of suture connected to the body. The anchor may include an aperture adapted to receive the length of suture. A method of using the sizer is provided that includes grasping the sizer with an instrument and positioning the sizer adjacent to a valve into a position suitable to allow for measurement of the valve.

17 Claims, 5 Drawing Sheets

(56) References Cited

U.S. PATENT DOCUMENTS

| | | | |
|---|---|---|---|
| 6,019,739 A * | 2/2000 | Rhee et al. | 606/148 |
| 7,258,698 B2 * | 8/2007 | Lemmon | 623/2.11 |
| 2002/0020074 A1 | 2/2002 | Love et al. | |
| 2009/0132036 A1 * | 5/2009 | Navia | 623/2.36 |
| 2009/0192600 A1 * | 7/2009 | Ryan | 623/2.11 |
| 2009/0192606 A1 * | 7/2009 | Gloss et al. | 623/2.36 |

FOREIGN PATENT DOCUMENTS

| | | |
|---|---|---|
| JP | 2009077838 A | 4/2009 |
| WO | 9302640 | 2/1993 |
| WO | 96/39942 A1 | 12/1996 |
| WO | 99/65423 A1 | 12/1999 |
| WO | 01/19291 A1 | 3/2001 |
| WO | 2009/067519 A2 | 5/2009 |

OTHER PUBLICATIONS

Japanese Office Action for Application No. 2011-549151 dated Nov. 29, 2013.

* cited by examiner

ROBOTIC HEART VALVE ANNULUS SIZER

CROSS-REFERENCE TO RELATED APPLICATIONS

This application is a national phase entry under 35 U.S.C. §371 of International Application No. PCT/US2010/000273, filed Feb. 1, 2010, published in English, which claims the benefit of the filing date of U.S. Provisional Patent Application No. 61/206,970, filed Feb. 6, 2009, the disclosure of which is hereby incorporated herein by reference.

FIELD OF THE INVENTION

The present invention relates to devices and methods for sizing a heart valve annulus, and more particularly to heart valve annulus sizers adapted to be used in connection with a suture to prevent misplacement or loss of the sizer.

BACKGROUND OF THE INVENTION

During a cardiac valve repair, an annuloplasty ring may be implanted as part of the valve repair to reshape the diseased valve and annulus, bringing the valve back to its natural anatomical shape. The ring also provides support to the annulus by preventing subsequent annulus dilatation once the valve has been repaired.

Annuloplasty rings are typically formed in different sizes which generally correspond to the different sizes of valve annulus from one patient to the next. In order to determine which size of annuloplasty ring to use for a particular patient, the surgeon frequently employs a sizer to approximate the current size of the valve annulus. The surgeon inserts the sizer adjacent to and in alignment with the valve annulus and visualizes whether the annulus is bigger or smaller than the sizer. This procedure may be performed several times with different sizers until a sizer which most closely corresponds to the size of the valve annulus has been determined.

As these repair procedures may be performed through small incision ports, the surgeon's ability to visualize the surrounding anatomy is often limited. The nature of the location of the valve repair as well as the small size of the anatomy and repair items makes it difficult for a surgeon to easily guide and place objects, such as annuloplasty rings and annulus sizers, within the patient for measurement and implantation. Furthermore, the small size of such objects poses a potential threat to the patient, as such objects may be mishandled, misplaced, or lost in the patient due to error on the part of the surgeon and/or the robot performing the surgical procedure.

Therefore, a need exists for a device for sizing a heart valve annulus that allows a surgeon greater and more accurate control over the surgical procedure and that provides a safety means for recovering a misplaced or lost device within the patient.

BRIEF SUMMARY OF THE INVENTION

A first aspect of the present invention is a heart valve annulus sizer including a body having a peripheral portion defining an opening through the body, at least one rib disposed within the opening and dividing the opening into at least a first opening and a second opening, and an anchor disposed on and projecting from the body.

In accordance with certain embodiments of this first aspect, the anchor may have an aperture adapted to receive a length of suture. The body may have a top surface and the anchor may be disposed on the top surface. The anchor may be disposed on the peripheral portion of the body. The body may have a top surface and a bottom surface, and the anchor may project from the peripheral portion in a direction substantially parallel to the top surface. The body may include two ribs each having first and second ends connected to the peripheral portion, and the two ribs may divide the opening in the body into three openings. The at least one rib may include first and second ends connected to the peripheral portion. The at least one rib may include a first rib having first and second ends connected to the peripheral portion, and a second rib having first and second ends, and at least one of the first and second ends of the second rib may be connected to the first rib. The peripheral portion may include an anterior side, a posterior side, and at least one notch in the anterior side for alignment with the tissue adjacent to a trigone in the valve. The at least one rib may include an end that is connected to the peripheral portion adjacent to the at least one notch. The peripheral portion may include an anterior side, a posterior side, and a notch in the posterior side for alignment with the anterior leaflet of the mitral valve. The body may have a top surface and indicia disposed on the top surface. The sizer may be constructed of a material selected from the group consisting of titanium, stainless steel, MP35N, Elgiloy, Platinum, Tantalum, and combinations thereof. The sizer may include a radiopaque material.

A second aspect of the present invention is a heart valve annulus sizer including a body having a peripheral portion defining an opening through the body, at least one rib disposed within the opening and dividing the opening into at least a first opening and a second opening, an anchor disposed on and projecting from the body, and a length of suture connected to the body.

In accordance with certain embodiments of this second aspect, the length of suture may be connected to at least one of a portion of the peripheral portion, one or more of the at least one rib, and the anchor.

A third aspect of the present invention is a method of sizing a heart valve annulus including the steps of providing a heart valve annulus sizer including a body having a peripheral portion defining an opening through the body, at least one rib disposed within the opening and dividing the opening into at least a first opening and a second opening, an anchor disposed on and projecting from the body, and a length of suture connected to the body, grasping the sizer with a forceps, and positioning the sizer adjacent to the valve into a position suitable to allow for measurement of the valve.

In accordance with certain embodiments of this third aspect, the method may further include the steps of selecting an annuloplasty ring according to the measurement taken by the sizer and inserting and securing the annuloplasty ring into the valve. The method may further include the step of removing the sizer from the patient by pulling on the ends of the suture to manipulate the sizer.

A fourth aspect of the present invention is a method of preparing a sizer for sizing a heart valve annulus including the steps of providing a heart valve annulus sizer including a body having a peripheral portion defining an opening through the body, at least one rib disposed within the opening and dividing the opening into at least a first opening and a second opening, and an anchor disposed on and projecting from the body, the anchor having an aperture, providing a length of suture, and connecting the length of suture to the body.

In accordance with certain embodiments of this fourth aspect, the step of connecting may further include attaching the length of suture to the sizer by looping the length of suture around at least one of a portion of the peripheral portion, one or more of the at least one ribs, and the anchor by way of the aperture.

Due to the varying size and shape of the cardiac valve being repaired in a given patient, using a sizer or obturator to obtain dimensional information about the patient's valve during a robotic repair procedure could ensure that a surgeon selects the most appropriately sized annuloplasty ring. Using a radiopaque sizer may be beneficial because the sizer may be located with imaging techniques if the sizer becomes disengaged from the robotic forceps and migrates away from the surgeon's field of view.

To prevent the sizer from disengaging from the surgical robot forceps or migrating out of view, features of the sizer may include: i) a raised anchor to a) facilitate the placement of a suture around the anchor, by looping the suture through an opening in the anchor, and permitting the suture to extend out of the patient's body, and b) permit the sizer to be grasped by robotic forceps during a robotic surgical repair procedure; and ii) at least two ribs within the sizer to provide structural support to the sizer and to provide a grasping feature for the surgical robot forceps. To aid in the implantation of an annuloplasty ring during a valve repair procedure, features of the sizer may include: i) at least two ribs within the sizer to guide identification of the trigones of the valve (for a mitral valve) or commissures of the valve (for a tricuspid valve); and ii) at least one opening through the sizer to permit visualization of the valve beneath the sizer during the repair procedure.

DETAILED DESCRIPTION

Figure 1:
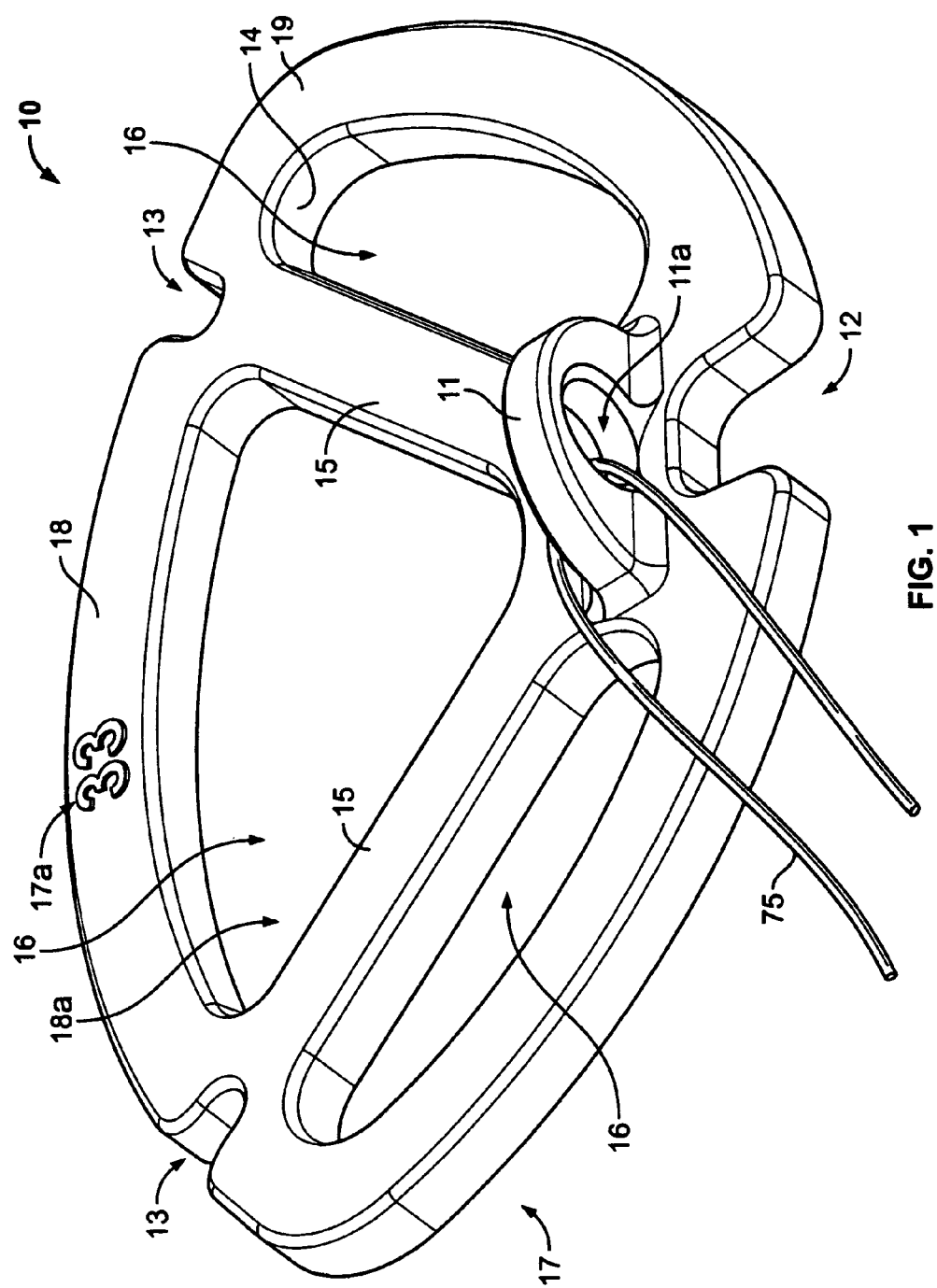
FIG. 1 is a perspective view of a sizer in accordance with an embodiment of the present invention.
Figure 2:
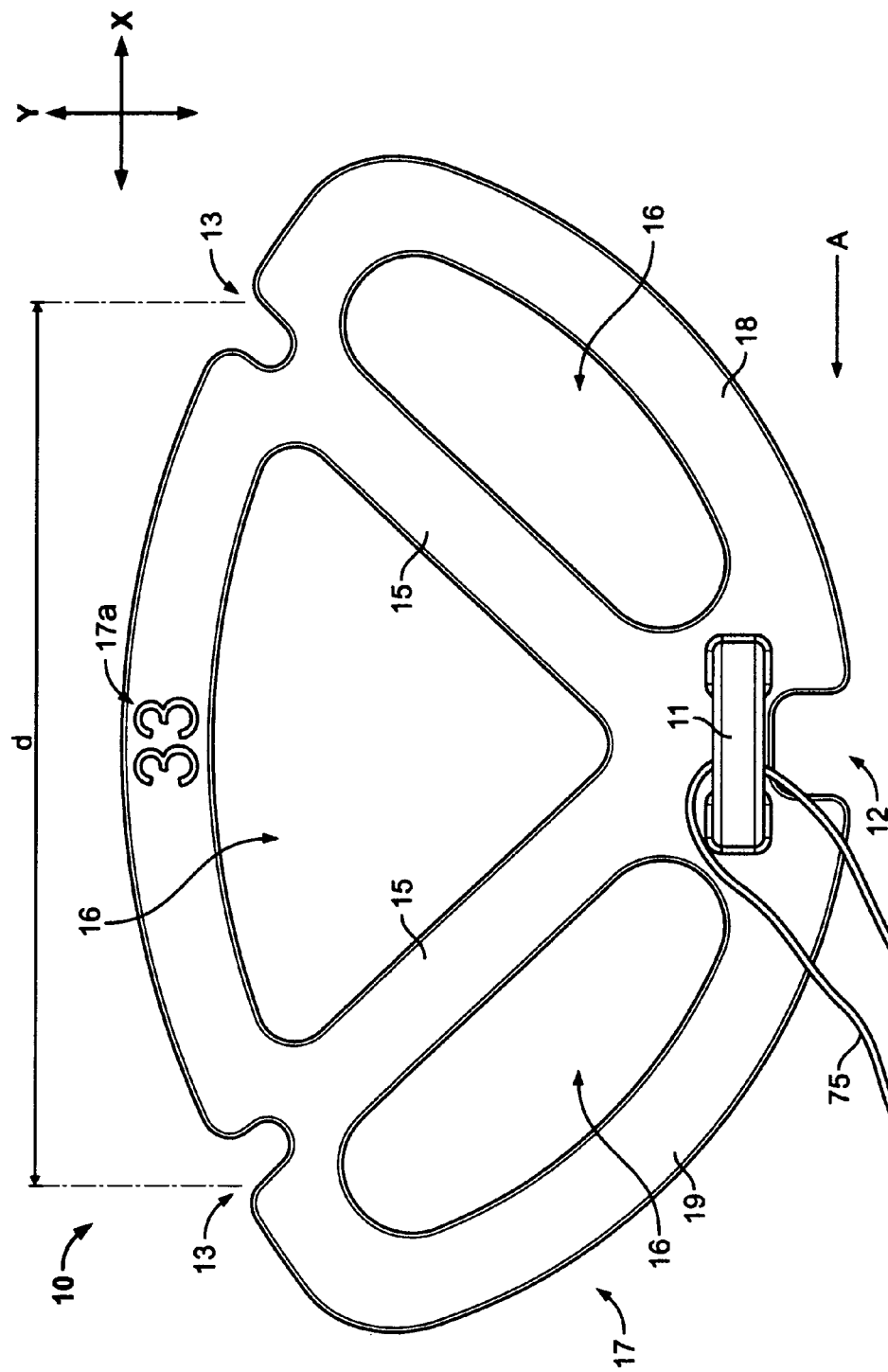
FIG. 2 is a plan view of the sizer shown in FIG. 1.

Referring to the drawings, FIGS. 1-5 show embodiments of a sizer having an anchor feature in accordance with the present invention, as well as variants thereof. FIGS. 1 and 2 show a sizer 10 in accordance with a first embodiment of the present invention. Sizer 10 includes a body 17 and an anchor 11. Body 17 includes a peripheral portion 18 that defines an opening 18a. Body 17 further includes two ribs 15 that are disposed within the opening and connected at each end to peripheral portion 18. The cross-section of the peripheral portion and ribs of the sizer may be round, square, or any other shape. Ribs 15 divide opening 18a into three smaller openings 16 within body 17. Of course, any appropriate number of ribs and corresponding openings may be included in body 17. Ribs 15 may also be oriented within the peripheral portion in any manner which provides support to the body. Openings 16 maximize visualization of the valve below sizer 10 during sizing of the annulus by allowing the surgeon to see through sizer 10 to sense the relative anatomic position of the valve beneath the sizer. Anchor 11 forms an aperture 11a which may be disposed entirely within anchor 11 or positioned between anchor 11 and body 17. Anchor 11 may be configured in a semi-circular shape or any other shape that allows for the formation of aperture 11a. Further, anchor 11 may be formed without an aperture, as explained below.

Body 17 has a top surface 19 and a bottom surface (not shown) with a thickness 14 defined therebetween. Either or both of top surface 19 and the bottom surface may be substantially planar or otherwise curved. Thickness 14 may be substantially constant or may vary throughout body 17. In a preferred embodiment, both the top and bottom surfaces of the sizer are substantially planar and the thickness between the surfaces is substantially constant, thereby defining a sizer which is substantially flat. The edges at the mating surfaces of sizer 10 are preferably rounded for ease of grasping portions of body 17 with an instrument, to improve their visibility in a projected image of the surgical site, to avoid damaging or compressing the annulus tissue when same is contacted by sizer 10, and to avoid fracturing the edges of the sizer when grasped by an instrument.

Disposed about the periphery of body 17 are a leaflet notch 12 and two trigonal notches 13, as shown in FIGS. 1 and 2. Leaflet notch 12 is positioned on the posterior side of sizer 10 and permits a surgeon to grasp the anterior leaflet of the mitral valve underneath sizer 10 to estimate, for example, the area of the anterior leaflet. Such estimation may be performed by a surgeon during a repair procedure to better determine whether sizer 10 approximates the size of the valve. Trigonal notches 13 serve as markers and are positioned on the anterior side of sizer 10. In the mitral valve, the tissue in the area of the trigones is thick and fibrous. Trigonal notches 13 allow the surgeon to visualize the trigones and align sizer 10 with the position of the trigones to more accurately size the valve during the repair procedure. A distance d (shown in FIG. 2) is shown between trigonal notches 13 which corresponds to the size of sizer 10, also indicated by indicia 17a.

As shown in FIGS. 1 and 2, ribs 15 are substantially aligned at one end with trigonal notches 13 to draw the surgeon's attention to the location of trigonal notches 13 and therefore aid in the alignment of sizer 10 with the trigones. Such an orientation of the ribs is preferable, though not necessary. Ribs 15 also provide structural support within body 17. Ribs 15, peripheral portion 18, and anchor 11 may be dimensioned for grasping by forceps or another surgical tool during a surgical procedure.

As shown in FIGS. 1 and 2, sizer 10 includes indicia 17a that represents the size of sizer 10. Indicia 17a may be positioned, for example, on top surface 19 of sizer 10. Indicia 17a may be raised from top surface 19, recessed in top surface 19, printed on sizer 10, or applied thereto in any other way known in the art. Of course, indicia 17a is for the benefit of the surgeon and may be located in any suitable location on sizer 10. One or more indicia may be present on a sizer. In FIGS. 1 and 2, sizer 10 has indicia 17a listing the size as "33." Other possible sizes may include, but are not limited to, 23, 25, 27, 29, 31, 35, 37, or 39, which size refers to a particular dimension in millimeters of sizer 10 and/or a corresponding annuloplasty ring.

Sizer 10 is configured to receive a suture 75 looped through aperture 11a of anchor 11 (as shown in FIG. 1). In embodiments in which anchor 11 does not include an aperture 11a, or depending on the preference of the surgeon, suture 75 may be looped around one or more ribs 15 or around a portion of peripheral portion 18. Regardless of how suture 75 is engaged with sizer 10, the ends of suture 75 may extend outside of the patient's body to permit the surgeon to retrieve sizer 10 if the positioning or location of sizer 10 is unintentionally moved or displaced during a procedure or if sizer 10 is dropped inside the patient. The surgeon may manipulate the ends of suture 75 to reposition sizer 10 if the sizer cannot be easily grasped by another instrument (e.g., robotic forceps).

In a variant thereof, sizer 10 may be provided without leaflet notch 12. Optionally, sizer 10 may also be provided without trigonal notches 13. Such notches are included for the aid of the surgeon. There may be more or fewer notches incorporated into the sizer according to the particular needs of the surgeon or procedure, or for purposes of simplifying manufacture of the sizer.

As shown in FIG. 2, anchor 11 may be oriented such that an instrument, such as robotic forceps or another surgical instrument, may grasp sizer 10 from a direction A that is substantially aligned with anchor 11 and parallel with a horizontal, or X, axis of the sizer. Alternatively, anchor may be positioned in a vertical orientation which is parallel with a vertical, or Y, axis of the sizer. The orientation of the anchor on the sizer may be dictated by the manner in which the repair procedure is performed, or the direction from which the instrument may approach the anchor to manipulate the sizer. Thus, anchor 11 may be oriented at any angle relative to the horizontal and vertical axes of the sizer that will facilitate the surgical procedure.

Figure 3:
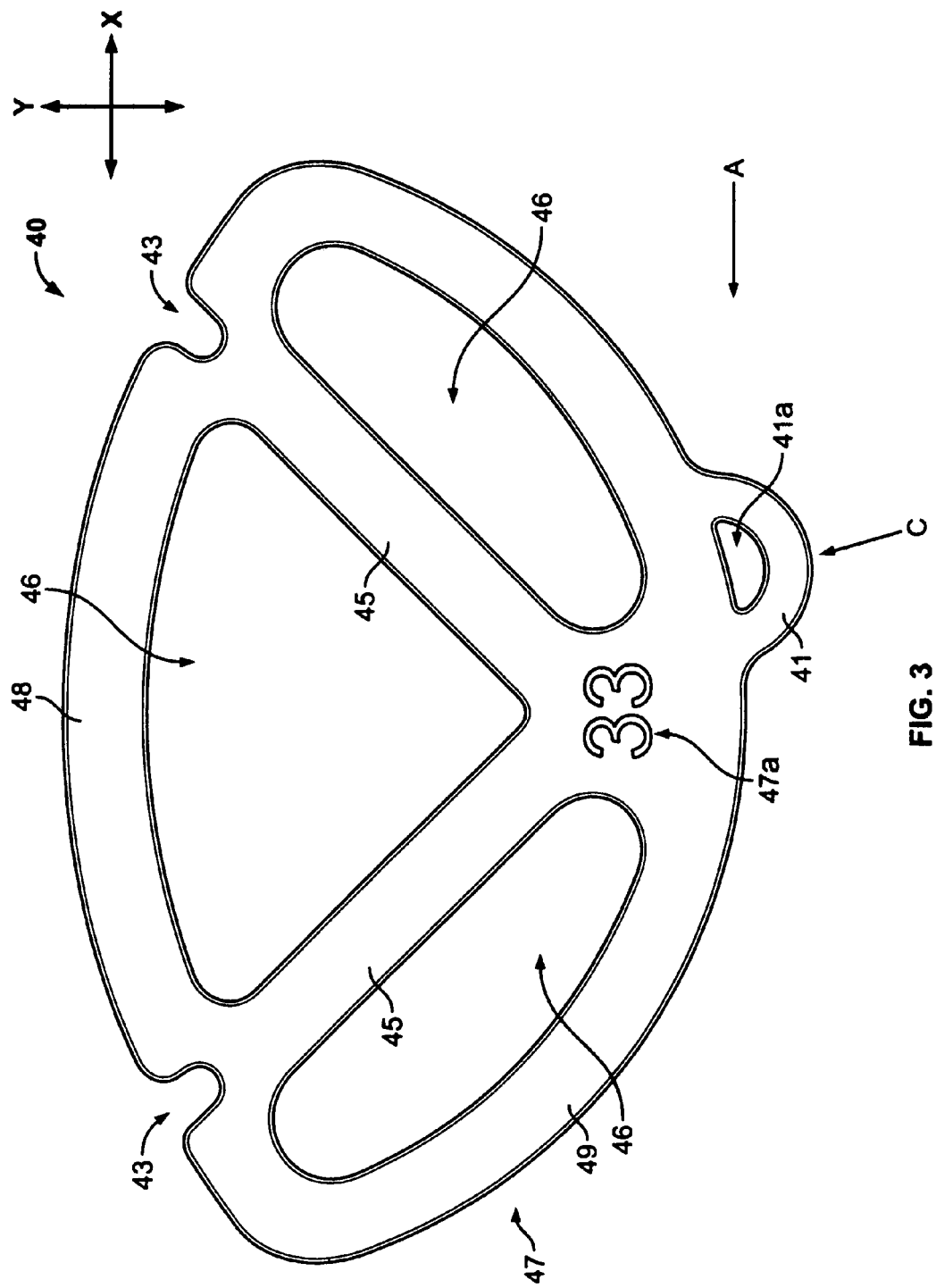
FIG. 3 is a plan view of a sizer in accordance with another embodiment of the present invention.
Figure 4:
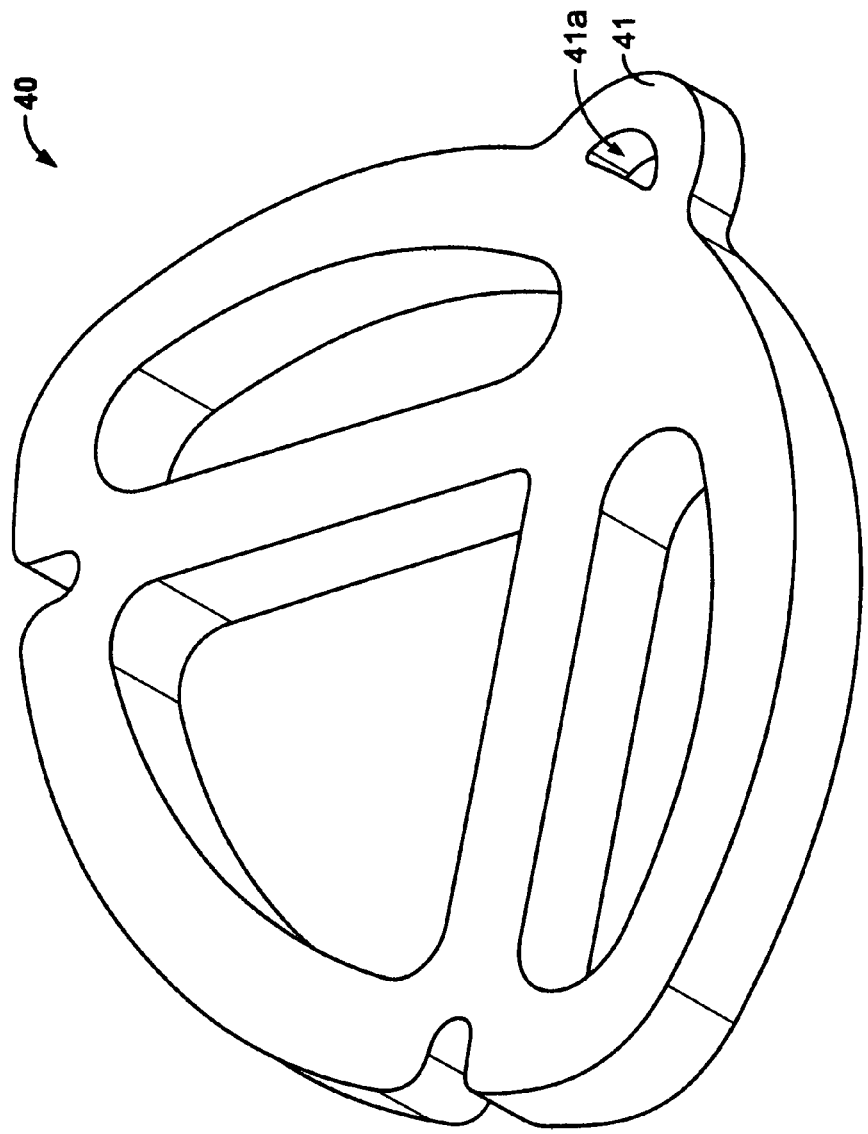
FIG. 4 is a perspective view of the sizer shown in FIG. 3.

FIGS. 3 and 4 show a sizer 40 according to another embodiment of the present invention. Sizer 40 is substantially the same as sizer 10 described above, and includes a body 47 having a peripheral portion 48, a top surface 49, and a bottom surface (not shown). However, rather than having an anchor projecting from the top surface of the sizer as in sizer 10, sizer 40 has an anchor 41 projecting laterally from peripheral portion 48 so as to be bounded by planes that include top surface 49 and the bottom surface of body 47. Aperture 41a in anchor 41 is thus oriented substantially normal to top surface 49. Anchor 41 may be positioned to facilitate an approach of forceps from direction A, parallel with the X axis, or from a direction C that may form any suitable angle with the X axis. Thus, while FIGS. 3 and 4 illustrate anchor 41 in a position near the center of the larger side of sizer 40, anchor 41 may be positioned anywhere along the peripheral portion 48 thereof that will facilitate the surgical procedure. FIG. 3 also shows trigonal notches 43, ribs 45, openings 46, and indicia 47a, each of which is substantially similar to the counterparts of sizer 10.

Figure 5:
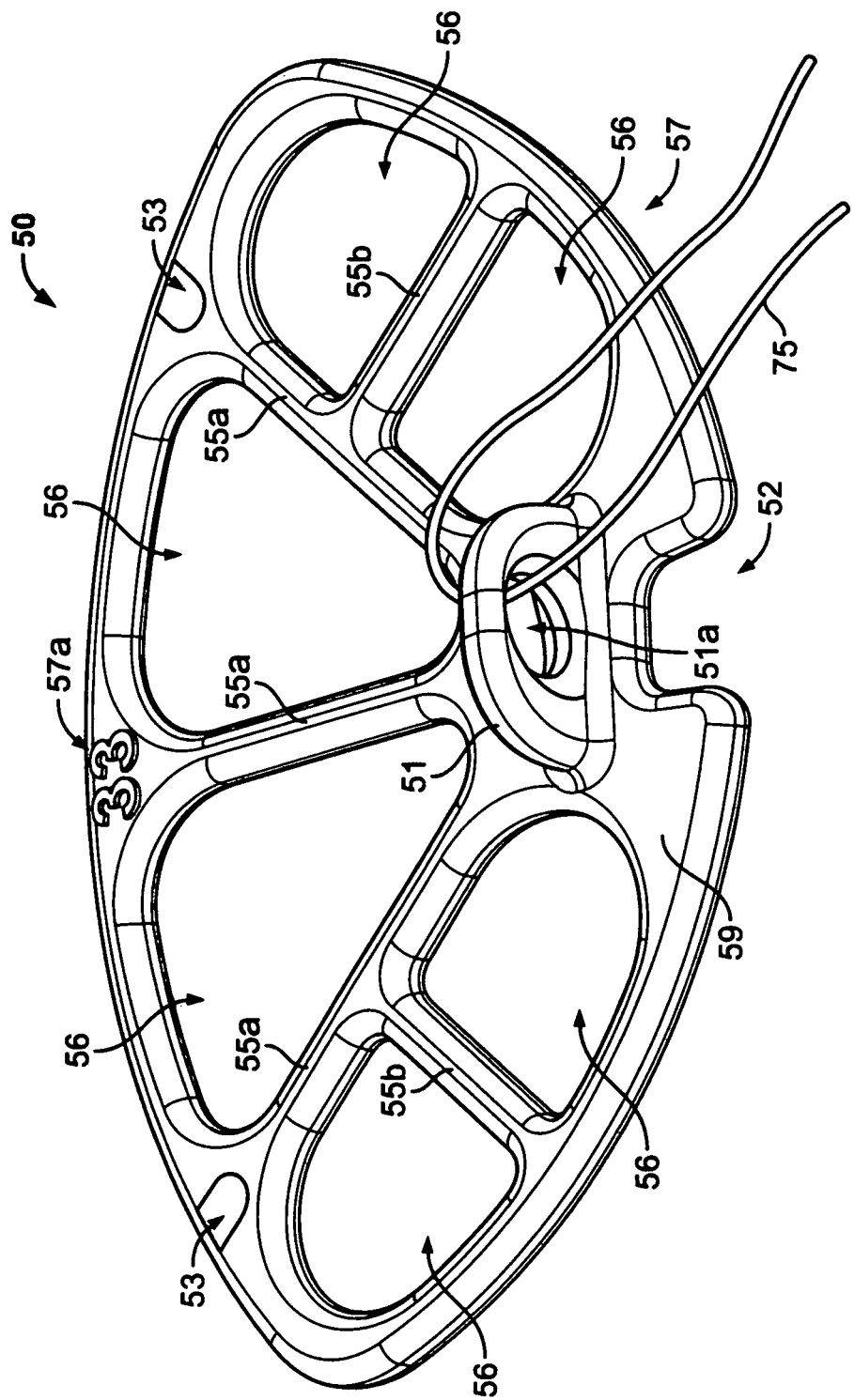
FIG. 5 is a perspective view of a sizer in accordance with another embodiment of the present invention.

FIG. 5 shows a sizer 50 in accordance with another embodiment of the present invention. Sizer 50 is similar to sizers 10 and 40 described above, and may include any or all of the features thereof, such as a leaflet notch 52, trigonal notches 53, and openings 56. Rather than the two ribs of sizers 10 and 40, sizer 50 includes multiple ribs 55a and 55b to increase the number of positions at which a grasping implement may grasp sizer 50 and the number of directions from which the grasping implement may approach sizer 50 to manipulate the orientation of sizer 50 relative to the annulus. Ribs 55a and 55b are also oriented to strengthen and support body 57. As shown in FIG. 5, first ribs 55a are connected at each end to portions of peripheral portion 58, and second ribs 55b are connected at one end to peripheral portion 58 and at the other end to one of first ribs 55a. Ribs 55a and 55b are indicative of the various orientations of ribs within the body of a sizer according to the present invention. More or fewer ribs may be included for purposes of strength and ease of grasping the sizer during a surgical procedure.

Sizer 50 also may include an anchor 51 which is similar to anchor 11 in that it protrudes from body 57 in a direction substantially perpendicular to top surface 59 of sizer 50 and may be oriented such that an instrument, such as robotic forceps, may approach sizer 50 from any suitable direction to grasp anchor 51 and move sizer 50. Alternatively, anchor 51 may protrude laterally from peripheral portion 58, similar to anchor 41 of sizer 40. The position and orientation of anchor 51 on sizer 50 may be dictated by the manner in which the robotic repair procedure is performed, or the direction from which the robotic forceps may approach anchor 51 to move sizer 50. Anchor 51 may include an aperture 51a for receiving a suture 75 therethrough, as shown in FIG. 5, or may be formed without an aperture.

As shown in FIGS. 1 and 5, suture 75 is positioned within the aperture of the anchor. As mentioned above, suture 75 may also be looped around a rib or another portion of the body of the sizer. One or more sutures may be used by the surgeon. The suture has a length such that the ends of the suture extend outside the body of the patient during a surgical procedure. The ends of the suture may be tied together or may remain loose. Either or both of the ends of the suture may be tied to an instrument or otherwise connected to the surgeon, or they may remain free. Should the sizer become lost or displaced during a surgical procedure, the ends of the suture should be accessible to the surgeon so that the suture can be pulled to retrieve the sizer from the patient.

Sizers according to the present invention may be comprised of any suitable material, such as titanium, stainless steel, MP35N, Elgiloy, platinum, tantalum, or combinations thereof. Alternatively, the sizers may be formed of a transparent material, such as a transparent polymer. A suitable material is preferably capable of withstanding the force imposed by a robot or surgeon through a grasping instrument such as forceps. As an additional patient safety measure, a sizer according to the present invention also may include a radiopaque material to enable the sizer to be identified within the patient by a suitable imaging technique, such as x-ray imaging. The sizer may be formed entirely or partially from the radiopaque material, or the sizer may include regions of radiopaque material, such as regions 53 depicted on sizer 50. The radiopaque material allows the sizer to be detected and located if the sizer disengages from the surgical robot or grasping instrument or otherwise migrates away from the surgeon's field of view.

The overall shape of the sizers may mimic the natural anatomical shape of the repaired cardiac valve, and may include a D-shape or an oval shape. Sizers may have any suitable thickness for sizing the annulus while also being clearly visible in a projected image of the surgical site.

Any of the sizers according to the present invention may be used during a robotic surgical procedure to repair a cardiac valve. The following procedure will be described with respect to sizer 10. While the present invention may be used in various cardiac valve repair procedures, a mitral valve procedure is described herein, as it serves as a useful context in which to illustrate the invention.

The procedure may involve creating four small incisions in the patient to permit insertion of three robotic arms and a camera. At least one of the robotic arms includes a forceps to grasp and manipulate tissue and to grasp the sizer. In addition, an incision may be made in the patient that exposes at least the appropriate atrium of the heart, the incision being sufficiently large to permit insertion of sizer 10 into the patient. A camera may be used to observe the surgical site (e.g., the valve) and permit the surgeon to visualize the sizing of the annulus with sizer 10 and repair the valve using an annuloplasty ring.

Before sizer 10 is placed in the atrium to size the annulus, the surgeon may perform any other suitable steps of the repair procedure. For example, the length of the chordae attached to the affected valve may be adjusted using artificial suture strands to set the coaptation length of the valve leaflets. The ventricle beneath the affected valve may be pressurized by filling with saline to examine the coaptation of the leaflets.

The surgeon may focus on adjusting the posterior portion of the valve, such as the P3 segment.

Once the surgeon has repaired the valve to its natural anatomical shape or has adjusted the annulus to the desired size and shape, the surgeon may loop suture 75 through aperture 11a or around rib 15 or peripheral portion 18 of sizer 10 with the ends of suture 75 extending outside of the patient's body so as to permit the surgeon to retrieve sizer should it disengage from the forceps. Sizer 10 may alternatively be provided to the surgeon prepackaged with suture 75 threaded through aperture 11a of anchor 11. A robotic forceps may grasp any rib 15 without interfering with the suture. Sizer 10 may be grasped at anchor 11, a rib 15, or peripheral portion 18 by the robotic forceps. The surgeon manipulates sizer 10 to the desired valve position in order to size the valve annulus and determine which size of annuloplasty ring to use. Sizer 10 then is removed from the annulus before the annuloplasty ring is introduced into the atrium, but the annuloplasty ring is aligned with the position outlined by sizer 10. The annuloplasty ring is then sewn onto the annulus on the atrial side of the valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

INDUSTRIAL APPLICABILITY

The present invention enjoys wide industrial applicability including, but not limited to, systems and methods for sizing heart valve annuluses.

The invention claimed is:

1. A heart valve annulus sizer, comprising:
a body having a top surface, a bottom surface, and a peripheral portion defining an opening through the body, the peripheral portion having an anterior side and a posterior side;
at least one notch in the anterior side of the peripheral portion extending through the top surface and the bottom surface;
at least one rib disposed within the opening and dividing the opening into at least a first opening and a second opening, the at least one rib having a longitudinal axis along a length of the rib, the longitudinal axis intersecting the at least one notch; and
an anchor disposed on and projecting from the body.

2. The heart valve annulus sizer of claim 1, wherein the anchor includes an aperture adapted to receive a length of suture therethrough.

3. The heart valve annulus sizer of claim 1, wherein the anchor is disposed on the top surface of the body.

4. The heart valve annulus sizer of claim 1, wherein the anchor is disposed on the peripheral portion of the body.

5. The heart valve annulus sizer of claim 1, wherein the anchor projects from the peripheral portion in a direction substantially parallel to the top surface of the body.

6. The heart valve annulus sizer of claim 1, wherein the body includes two ribs each having first and second ends connected to the peripheral portion, the two ribs dividing the opening in the body into three openings.

7. The heart valve annulus sizer of claim 1, wherein the at least one rib includes a first rib having first and second ends connected to the peripheral portion, and a second rib having first and second ends, at least one of the first and second ends of the second rib being connected to the first rib.

8. The heart valve annulus sizer of claim 1, wherein the annulus sizer is for sizing the annulus of the mitral valve, and the at least one notch is configured for alignment with tissue adjacent to a trigone of the mitral valve.

9. The heart valve annulus sizer of claim 1, wherein the annulus sizer is for sizing the annulus of the mitral valve, the sizer further comprising another notch in the posterior side configured for alignment with the anterior leaflet of the mitral valve.

10. The heart valve annulus sizer of claim 1, wherein the body has indicia disposed on the top surface.

11. The heart valve annulus sizer of claim 1, wherein the sizer is constructed of a material selected from the group consisting of titanium, stainless steel, MP35N, Elgiloy, Platinum, Tantalum, and combinations thereof.

12. The heart valve annulus sizer of claim 1, wherein the sizer includes a radiopaque material.

13. The heart valve annulus sizer of claim 1, further comprising a length of suture connected to the body.

14. A method of sizing a heart valve annulus, the method comprising the steps of:
providing a heart valve annulus sizer including a body having a top surface, a bottom surface, and a peripheral portion defining an opening through the body, the peripheral portion having an anterior side and a posterior side, at least one notch in the anterior side of the body extending through the top surface and the bottom surface, at least one rib disposed within the opening and dividing the opening into at least a first opening and a second opening, the at least one rib having a longitudinal axis along a length of the rib, the longitudinal axis intersecting the at least one notch, an anchor disposed on and projecting from the body, and a length of suture connected to the body;
grasping the sizer with a forceps; and
positioning the sizer adjacent to the valve in a position suitable to allow for measurement of the valve annulus.

15. The method of claim 14, further comprising the steps of:
selecting an annuloplasty ring according to the measurement taken by the sizer; and
inserting and securing the annuloplasty ring to the valve annulus.

16. The method of claim 14, further comprising the step of:
removing the sizer from the patient by pulling on the ends of the suture to manipulate the sizer.

17. The heart valve annulus sizer of claim 13, wherein the length of suture is connected to at least one of a portion of the peripheral portion, the at least one rib, or the anchor.

* * * * *